US012589769B2

(12) United States Patent
Harkleroad et al.

(10) Patent No.: US 12,589,769 B2
(45) Date of Patent: Mar. 31, 2026

(54) MOTION SICKNESS MITIGATION

(71) Applicant: Toyota Motor Engineering & Manufacturing North America, Inc., Plano, TX (US)

(72) Inventors: John D. Harkleroad, Ypsilanti, MI (US); Vasudeva S. Murthy, Ann Arbor, MI (US)

(73) Assignees: Toyota Motor Engineering & Manufacturing North America, Inc., Plano, TX (US); Toyota Jidosha Kabushiki Kaisha, Toyota (JP)

( * ) Notice: Subject to any disclaimer, the term of this patent is extended or adjusted under 35 U.S.C. 154(b) by 197 days.

(21) Appl. No.: 18/219,916

(22) Filed: Jul. 10, 2023

(65) Prior Publication Data

US 2025/0018979 A1 Jan. 16, 2025

(51) Int. Cl.

| | |
|---|---|
| ***B60W 60/00*** | (2020.01) |
| ***A61B 5/00*** | (2006.01) |
| ***A61B 5/05*** | (2021.01) |
| ***A61B 5/11*** | (2006.01) |
| ***B60H 1/00*** | (2006.01) |
| ***B60J 3/04*** | (2006.01) |
| ***B60N 2/02*** | (2006.01) |

(52) U.S. Cl.

CPC ........... *B60W 60/0013* (2020.02); *A61B 5/05* (2013.01); *A61B 5/1114* (2013.01); *A61B 5/6893* (2013.01); *B60H 1/00742* (2013.01); *B60N 2/0278* (2023.08); *B60J 3/04* (2013.01); *B60W 2420/408* (2024.01); *B60W 2540/22* (2013.01)

(58) Field of Classification Search

None

See application file for complete search history.

(56) References Cited

U.S. PATENT DOCUMENTS

| | | | | |
|---|---|---|---|---|
| 9,868,332 | B2 * | 1/2018 | Anderson | B60G 99/002 |
| 10,107,635 | B2 * | 10/2018 | Larner | B60W 60/0013 |
| 10,942,037 | B1 * | 3/2021 | Larner | G05D 1/0088 |
| 11,529,090 | B2 | 12/2022 | Bulut et al. | |
| 11,541,797 | B2 | 1/2023 | Dhaens | |
| 11,585,670 | B2 * | 2/2023 | Larner | B60W 60/0013 |
| 2017/0136842 | A1 * | 5/2017 | Anderson | B60G 17/016 |
| 2018/0052000 | A1 * | 2/2018 | Larner | G05D 1/0212 |

(Continued)

OTHER PUBLICATIONS

D. Bresnahan and Y. Li, "Driver Head Motion Monitoring Using a mm-Wave FMCW Radar," 2021 IEEE Texas Symposium on Wireless and Microwave Circuits and Systems (WMCS), Waco, TX, USA, 2021, pp. 1-4, doi: 10.1109/WMCS52222.2021.9493294. (Year: 2021).*

(Continued)

*Primary Examiner* — Peter D Nolan
*Assistant Examiner* — Jacob Kent Besteman-Street
(74) *Attorney, Agent, or Firm* — Christopher G. Darrow; Darrow Mustafa PC

(57) ABSTRACT

Systems, methods, and other embodiments described herein relate to detecting whether a user in a vehicle is experiencing motion sickness. In one embodiment, a method includes determining whether a user in a vehicle is experiencing motion sickness based on a first movement measurement of the vehicle and a second movement measurement of a head of the user using a radar sensor and in response to determining whether the user is experiencing motion sickness, activating mitigation control.

18 Claims, 5 Drawing Sheets

(56) References Cited

U.S. PATENT DOCUMENTS

| | | | | |
|---|---|---|---|---|
| 2019/0022347 | A1 | 1/2019 | Wan et al. | |
| 2019/0204909 | A1* | 7/2019 | Xiao | G06F 3/0346 |
| 2020/0114929 | A1* | 4/2020 | Wan | A61B 5/02055 |
| 2020/0337623 | A1* | 10/2020 | Bulut | A61B 5/7275 |
| 2020/0383580 | A1* | 12/2020 | Shouldice | B60W 40/08 |
| 2020/0385025 | A1* | 12/2020 | Nishimura | B60W 60/0053 |
| 2022/0001893 | A1 | 1/2022 | Tartz | |
| 2022/0001894 | A1* | 1/2022 | Yeom | B60W 40/08 |
| 2022/0135054 | A1 | 5/2022 | Nakamura et al. | |
| 2022/0297577 | A1 | 9/2022 | Amereller et al. | |
| 2023/0305578 | A1* | 9/2023 | Melin | B60N 2/0276 |
| 2023/0339378 | A1* | 10/2023 | Takamatsu | B60N 2/0028 |
| 2024/0253414 | A1* | 8/2024 | Giovanardi | B60G 17/0195 |

OTHER PUBLICATIONS

M. Nosrati, S. Shahsavari, S. Lee, H. Wang and N. Tavassolian, “A Concurrent Dual-Beam Phased-Array Doppler Radar Using MIMO Beamforming Techniques for Short-Range Vital-Signs Monitoring,” in IEEE Transactions on Antennas and Propagation, vol. 67, No. 4, pp. 2390-2404, Apr. 2019 (Year: 2019).*

* cited by examiner

Head Movement = Vehicle Movement (In-Phase)

Head Movement (Out-of-Phase)

Vehicle Motion

440

450A  450C     450B

Phase Lag

Time

Motion Sickness Over Time

Cumulative Motion Sickness

460D

VERY HIGH

460C

HIGH

MEDIUM     460A

LOW

Time

MOTION SICKNESS MITIGATION

TECHNICAL FIELD

The subject matter described herein relates, in general, to systems and methods for determining whether a user in a vehicle is experiencing motion sickness.

BACKGROUND

The background description provided is to present the context of the disclosure generally. Work of the inventor, to the extent it may be described in this background section, and aspects of the description that may not otherwise qualify as prior art at the time of filing, are neither expressly nor impliedly admitted as prior art against the present technology.

Users travelling in a vehicle may experience motion sickness. Depending on the severity of the motion sickness, the effects may be debilitating for the users in the vehicle. Methods for detecting or predicting motion sickness can assist in minimizing the effect of motion sickness on the users in the vehicle.

SUMMARY

This section generally summarizes the disclosure and is not a comprehensive explanation of its full scope or all its features.

In one embodiment, a method for determining whether a user in a vehicle is experiencing motion sickness is disclosed. The method includes determining whether a user in a vehicle is experiencing motion sickness based on a first movement measurement of the vehicle and a second movement measurement of a head of the user using a radar sensor and in response to determining whether the user is experiencing motion sickness, activating mitigation control.

In another embodiment, a system for determining whether a user in a vehicle is experiencing motion sickness is disclosed. The system includes a processor and a memory in communication with the processor. The memory stores machine-readable instructions that, when executed by the processor, cause the processor to determine whether a user in a vehicle is experiencing motion sickness based on a first movement measurement of the vehicle and a second movement measurement of a head of the user using a radar sensor and in response to determining whether the user is experiencing motion sickness, activate mitigation control.

In another embodiment, a non-transitory computer-readable medium for determining whether a user in a vehicle is experiencing motion sickness and including instructions that, when executed by a processor, cause the processor to perform one or more functions, is disclosed. The instructions include instructions to determine whether a user in a vehicle is experiencing motion sickness based on a first movement measurement of the vehicle and a second movement measurement of a head of the user using a radar sensor and in response to determining whether the user is experiencing motion sickness, activate mitigation control.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Figure 1:
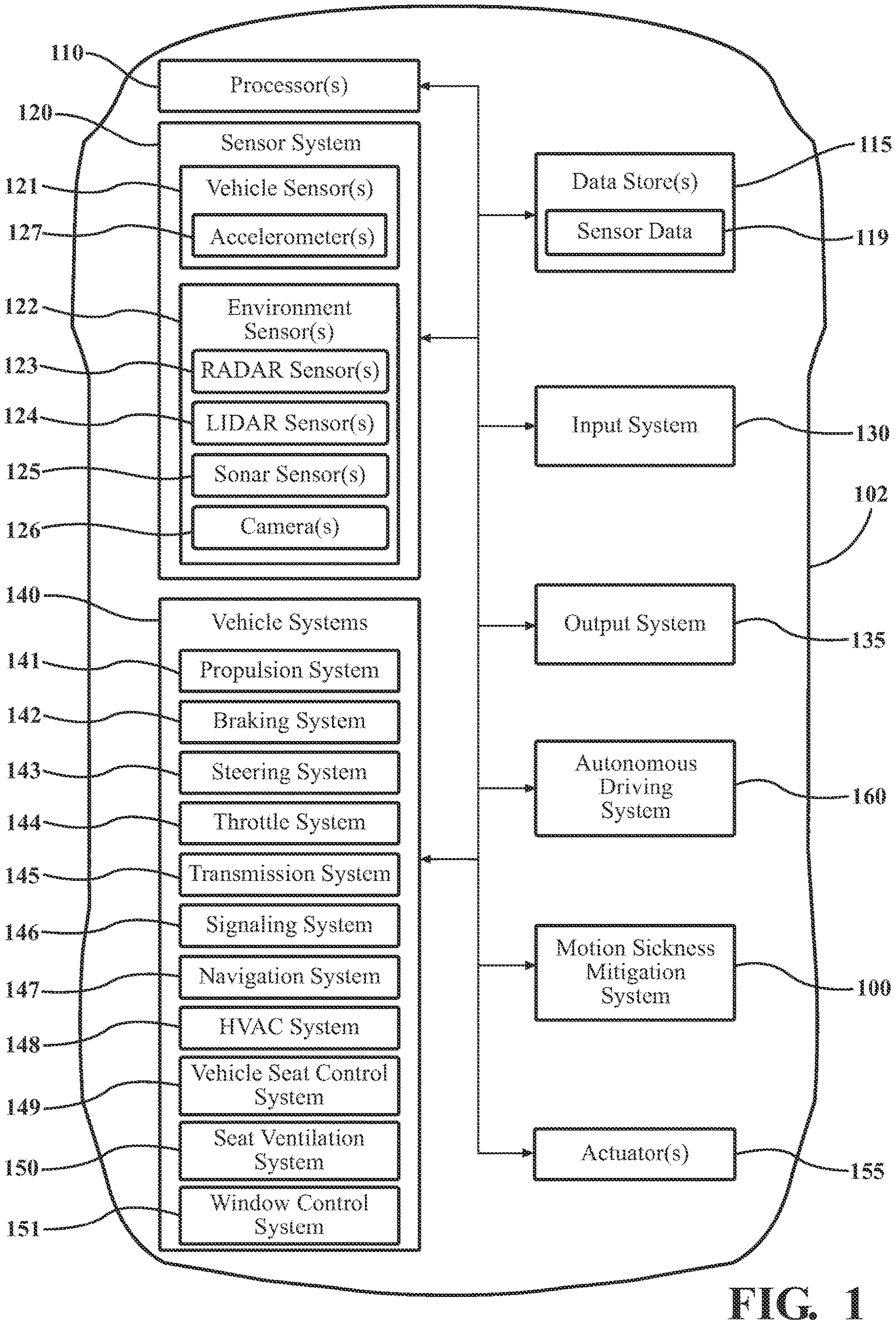
FIG. 1 illustrates a block diagram of a vehicle incorporating a motion sickness mitigation system.

Systems, methods, and other embodiments associated with determining whether a user in a vehicle is experiencing motion sickness, are disclosed. Additionally, the systems, methods, and other embodiments may determine the severity of the motion sickness and may alleviate the effects of the motion sickness using one or more mitigation measures.

Vehicle users may have varying sensitivity to motion sickness. Vehicle users may experience motion sickness in vehicles of any autonomous level, including autonomous vehicles, semi-autonomous, and manual vehicles. However, with the proliferation of autonomous vehicles, the vehicle users are likely to experience motion sickness and experience motion sickness with a more severity. As an example, motion sickness includes car sickness, air sickness, and/or sea sickness.

Accordingly, in one embodiment, the disclosed approach is motion sickness mitigation system that determines whether a user in a vehicle is experiencing motion sickness based on a first movement measurement of the vehicle and a second movement measurement of a head of the user using a radar sensor, and in response to determining whether the user is experiencing motion sickness, activates mitigation control.

The motion sickness mitigation system may be part of a vehicle. The vehicle may include a first sensor, such as a triaxial accelerometer, for detecting the first movement measurement of the vehicle. The vehicle may include a second sensor such as a radar sensor such as 60 GHz mm-wave radar for detecting the second movement measurement of the head of the user. The motion sickness mitigation system may determine the absolute movement measurement of the head of the user using the first movement measurement and the second movement measurement.

The motion sickness mitigation system includes a motion sickness incidence (MSI) model. As an example, the motion sickness mitigation system may develop the MSI model using AI and/or machine learning techniques. The MSI model is a predictive model that determines whether a user is experiencing motion sickness and if so, the severity of the motion sickness. The MSI model makes the determination based on the absolute movement measurement of the head of the user. The motion sickness mitigation system may also receive input information from the user indicating the user's motion sickness sensitivity level. The MSI model may also apply the input information from the user when determining whether the user is experiencing motion sickness and the severity of the motion sickness. The MSI model may consider the characteristics of the first movement measurement, the second movement measurement, and the absolute movement measurement. The characteristics may include the phrasal relationship, the amplitude, and the frequency of the movements.

The motion sickness mitigation system may further include mitigation measures. As an example, in the case where the vehicle is being used for shared rides, the motion sickness mitigation system may prioritize dropping off users with more severe motion sickness before users with less severe motion sickness. The motion sickness mitigation system may adjust one or more vehicle systems within the vehicle such as the vehicle cabin temperature, the tint of the windows, the opening of the windows, the vehicle seat recline angle, the air flow and/or air temperature of the seat ventilation system. The motion sickness mitigation system may apply these measures individually or in combination.

It will be appreciated that arrangements described herein can provide numerous benefits, including one or more of the benefits mentioned herein. For example, arrangements described herein assist in making vehicles and/or vehicle operators more responsive to the vehicle users experiencing motion sickness. Autonomous vehicles and/or vehicle operators can adjust the driving style such as reducing the speed, taking more gradual turns, travelling on a less bumpy road, adjusting the suspension settings, reducing abrupt braking, etc. Arrangements disclosed herein utilize relatively accessible hardware such as an accelerometer and a radar sensor. Arrangements described herein utilize triaxial movement measurements, which provide a more accurate prediction of motion sickness when compared to motion prediction systems based on a single axis.

Detailed embodiments are disclosed herein; however, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in the figures, but the embodiments are not limited to the illustrated structure or application.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details.

Referring to FIG. 1, a block diagram of a vehicle 102 incorporating a motion sickness mitigation system 100 is illustrated. The vehicle 102 includes various elements. It will be understood that in various embodiments, it may not be necessary for the vehicle 102 to have all of the elements shown in FIG. 1. The vehicle 102 can have any combination of the various elements shown in FIG. 1. Further, the vehicle 102 can have additional elements to those shown in FIG. 1. In some arrangements, the vehicle 102 may be implemented without one or more of the elements shown in FIG. 1. While the various elements are shown as being located within the vehicle 102 in FIG. 1, it will be understood that one or more of these elements can be located external to the vehicle 102. Further, the elements shown may be physically separated by large distances. For example, as discussed, one or more components of the disclosed system can be implemented within a vehicle while further components of the system can be implemented within a cloud-computing environment.

The vehicle 102 can include a sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can work independently from each other. Alternatively, two or more of the sensors can work in combination with each other. In such a case, the two or more sensors can form a sensor network. The sensor system 120 and/or the one or more sensors can be operatively connected to a processor(s) 110, a data store(s) 115, and/or another element of the vehicle 102 (including any of the elements shown in FIG. 1). The sensor system 120 can acquire data of at least a portion of the internal environment as well as the external environment of the vehicle 102.

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect, determine, and/or sense information about the vehicle 102 itself. In one or more arrangements, the vehicle sensor(s) 121 can be configured to detect, and/or sense position and orientation changes of the vehicle 102, such as, for example, based on inertial acceleration. In one or more arrangements, the vehicle sensor(s) 121 can include one or more accelerometers 127, one or more gyroscopes, one or more speedometers, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 102.

In one or more arrangements and as previously mentioned, the vehicle sensor(s) 121 may include one or more accelerometers 127. As an example, the accelerometer(s) 127 may be a triaxial accelerometer, capable of providing simultaneous measurements of all the vibrations the vehicle 102 is experiencing in three orthogonal directions.

In addition, the sensor system 120 can include one or more environment sensors 122 configured to acquire, and/or sense data inside the vehicle 102 as well as around the vehicle 102. Sensor data 119 inside the vehicle 102 can include information about one or more users (or occupants) in the vehicle cabin and any other objects of interest. Sensor data 119 around the vehicle 102 can include information about the external environment in which the vehicle 102 is located or one or more portions thereof.

As an example, the one or more environment sensors 122 can be configured to detect, quantify and/or sense objects in at least a portion of the internal and/or the external environment of the vehicle 102 and/or information/data about such objects.

In the internal environment of the vehicle 102, the one or more environment sensors 122 can be configured to detect, measure, quantify, and/or sense users inside the vehicle 102 and the position of the head(s) and/or shoulder(s) of the users. In the external environment, the one or more environment sensors 122 can be configured to detect, measure, quantify, and/or sense objects in the external environment of the vehicle 102.

Various examples of sensors of the sensor system 120 will be described herein. The example sensors may be part of the one or more environment sensors 122 and/or the one or more vehicle sensors 121. However, it will be understood that the embodiments are not limited to the particular sensors described.

As an example, in one or more arrangements, the sensor system 120 can include one or more radar sensors 123, one or more LIDAR sensors 124, one or more sonar sensors 125, and/or one or more cameras 126. In one or more arrangements, the one or more cameras 126 can be high dynamic range (HDR) cameras or infrared (IR) cameras. Any sensor in the sensor system 120 that is suitable for detecting and observing head movements of a user can be used inside the vehicle 102 to observe the user. The sensor system 120 may include a sensor that is capable of detecting and monitoring the head movements of a single user. Alternatively and additionally, the sensor system 120 may include a sensor that is capable of detecting and monitoring the head movements of multiple users, simultaneously or sequentially. The sensor may be a radar sensor 123.

As an example, the radar sensor 123 may be a 60 GHz radar, capable of measuring head movement in a low frequency range (e.g., between 0 and 2 Hz) with amplitude in the millimeter and/or centimeter range. The radar sensor 123 may be capable of identifying the head and shoulders of a user and then may track the head movements of the user. As an example, the radar sensor 123 may be mounted inside the vehicle 102 such that the user is in view of the radar sensor 123. The vehicle 102 may include multiple radar sensors 123. As an example, the vehicle 102 may include multiple radar sensors 123, where each radar sensor 123 is associated with a vehicle seat. As such, a 5-passenger vehicle 102 would have five radar sensors 123 with each radar sensor 123 is detecting the head movement of a user seated in a different vehicle seat.

In one embodiment, the vehicle 102 may include multiple accelerometers 127 and multiple radar sensors 123. As an example, one accelerometer 127 may be associated with and proximate to one radar sensor 123. As such, a 5-passenger vehicle 102 may have five accelerometers 127 and five radar sensors 123. Each accelerometer 127 and radar sensor 123 may be proximate to each other, and each pair of accelerometer 127 and radar sensor 123 may be proximate to a different vehicle seat. In another embodiment, the vehicle 102 may include fewer accelerometers 127 than radar sensors 123 and one accelerometer 127 may be utilized in relation to two or more radar sensors 123.

The vehicle 102 can include one or more vehicle systems 140. Various examples of the one or more vehicle systems 140 are shown in FIG. 1. However, the vehicle 102 can include more, fewer, or different vehicle systems 140. It should be appreciated that although particular vehicle systems are separately defined, each or any of the systems or portions thereof may be otherwise combined or segregated via hardware and/or software within the vehicle 102. The vehicle 102 can include a propulsion system 141, a braking system 142, a steering system 143, throttle system 144, a transmission system 145, a signaling system 146, a navigation system 147, a heating, ventilation, and air conditioning (HVAC) system 148, a vehicle seat control system 149, a seat ventilation system 150, and/or a window control system 151. Each of these systems can include one or more devices, components, and/or a combination thereof, now known or later developed. To further explain, the vehicle seat control system 149 may control and adjust a vehicle seat recline angle. The seat ventilation system 150 may control the ventilation system embedded in the vehicle seats. The seat ventilation system 150 may adjust the flow rate and/or the temperature of the air the ventilation system is outputting. The window control system 151 may control opening and/or closing the window. The window control system 151 may further control increasing and/or decreasing the tint of the window(s).

Some of the possible elements of the vehicle 102 are shown in FIG. 1 and will be described along with subsequent figures. However, a description of many of the elements in FIG. 1 will be provided after the discussion of FIGS. 2-4 for purposes of brevity of this description. Additionally, it will be appreciated that for simplicity and clarity of illustration, where appropriate, reference numerals have been repeated among the different figures to indicate corresponding or analogous elements. In addition, the discussion outlines numerous specific details to provide a thorough understanding of the embodiments described herein. Those of skill in the art, however, will understand that the embodiments described herein may be practiced using various combinations of these elements. In any case, as illustrated in the embodiment of FIG. 1, the vehicle 102 includes a motion sickness mitigation system 100 that is implemented to perform methods and other functions as disclosed herein relating to detecting whether a user is experiencing motion sickness and attempting to alleviate the effects of the motion sickness on the user. As an example, the motion sickness mitigation system 100, in various embodiments, may be implemented partially within the vehicle 102 and may further exchange communications with additional aspects of the motion sickness mitigation system 100 that are remote from the vehicle 102 in support of the disclosed functions. Thus, while FIG. 2 generally illustrates the motion sickness mitigation system 100 as being self-contained, in various embodiments, the motion sickness mitigation system 100 may be implemented within multiple separate devices some of which may be remote from the vehicle 102.

Figure 2:
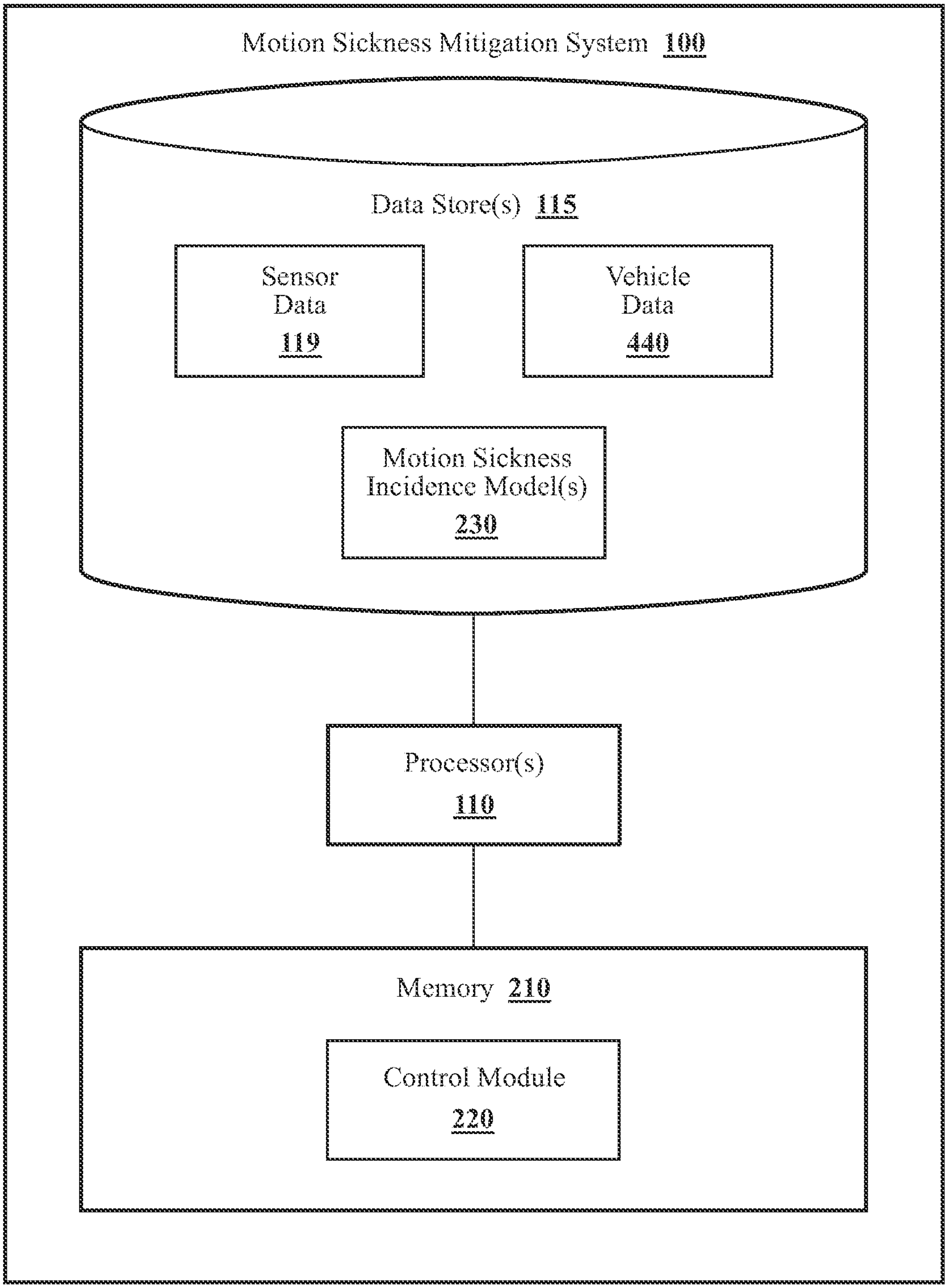
FIG. 2 is a block diagram of the motion sickness mitigation system of FIG. 1.

With reference to FIG. 2, a block diagram of the motion sickness mitigation system 100 is shown. The motion sickness mitigation system 100 may include a processor(s) 110. Accordingly, the processor(s) 110 may be a part of the motion sickness mitigation system 100, or the motion sickness mitigation system 100 may access the processor(s) 110 through a data bus or another communication pathway. In one or more embodiments, the processor(s) 110 is an application-specific integrated circuit that may be configured to implement functions associated with a control module 220. More generally, in one or more aspects, the processor(s) 110 is an electronic processor, such as a microprocessor that can perform various functions as described herein when loading the control module 220 and executing encoded functions associated therewith.

The motion sickness mitigation system 100 may include a memory 210 that stores the control module 220. The memory 210 may be a random-access memory (RAM), read-only memory (ROM), a hard disk drive, a flash memory, or other suitable memory for storing the control module 220. The control module 220 is, for example, computer-readable instructions that, when executed by the processor(s) 110, cause the processor(s) 110 to perform the various functions disclosed herein. While, in one or more embodiments, the control module 220 is a set of instructions embodied in the memory 210, in further aspects, the control module 220 includes hardware, such as processing components (e.g., controllers), circuits, etc. for independently performing one or more of the noted functions.

The motion sickness mitigation system 100 may include a data store(s) 115 for storing one or more types of data. Accordingly, the data store(s) 115 may be a part of the motion sickness mitigation system 100, or the motion sickness mitigation system 100 may access the data store(s) 115 through a data bus or another communication pathway. The data store(s) 115 is, in one embodiment, an electronically based data structure for storing information. In at least one approach, the data store 115 is a database that is stored in the memory 210 or another suitable medium, and that is configured with routines that can be executed by the processor(s) 110 for analyzing stored data, providing stored data, organizing stored data, and so on. In either case, in one embodiment, the data store 115 stores data used by the control module 220 in executing various functions. In one embodiment, the data store 115 may be able to store sensor data 119 and/or other information that is used by the control module 220.

The data store(s) 115 may include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 115 may be a component of the processor(s) 110, or the data store(s) 115 may be operatively connected to the processor(s) 110 for use thereby. The term "operatively connected" or "in communication with" as used throughout this description, can include direct or indirect connections, including connections without direct physical contact.

In one or more arrangements, the data store(s) 115 can include sensor data 119. The sensor data 119 can originate from the sensor system 120 of the vehicle 102. The sensor data 119 can include data from visual sensors and/or any other suitable sensors in the vehicle 102. More specifically, the sensor data 119 can include data from a radar sensor 123 capable of monitoring head movements of a user in the vehicle 102 and data from an accelerometer 127 capable of monitoring triaxial movements of the vehicle 102.

In one or more arrangements, the data store(s) 115 can include motion sickness incidence (MSI) model(s) 230. The MSI model 230 is a prediction model based on the head movements of the user relative to the ground. In other words, the MSI model 230 predicts whether a user is likely to experience motion sickness based on the head movements of the user relative to the earth. The MSI model 230 may further predict the severity of the motion sickness on the user. The MSI model 230 may be based on any suitable formula and/or method for predicting motion sickness and for further predicting the severity of the motion sickness. As an example, the MSI model 230 may be based on any suitable artificial intelligence or machine learning method.

In one embodiment, the control module 220 may include instructions that, when executed by the processor(s) 110, cause the processor(s) 110 to determine whether a user in a vehicle 102 is experiencing motion sickness based on a first movement measurement of the vehicle and a second movement measurement of a head of the user using a radar sensor 123. The motion sickness may be car sickness, air sickness, and/or sea sickness.

The control module 220 may request and/or receive the first movement measurement of the vehicle 102 from a suitable sensor. The first movement measurement may be based on one or more of a movement measurement, a velocity measurement, or an acceleration measurement. The movement measurement is based on the position and/or a change in position of the vehicle. The velocity measurement is based on the change in position of the vehicle as a function of time and the acceleration measurement is based on the rate of change in position of the vehicle as a function of time.

The first movement measurement of the vehicle 102 may be triaxial. As such, the first movement measurement of the vehicle 102 may include a displacement, a velocity rate, and/or an acceleration rate of the vehicle 102 along the three axes. As an example, a triaxial accelerometer 127 located in the vehicle 102 can measure the first movement measurement of the vehicle 102. The triaxial accelerometer 127 may then transmit the first movement measurement as a function of time to the control module 220.

The control module 220 may request and/or receive the second movement measurement of the head of the user from a radar sensor 123. The second movement measurement may be based on one or more of a movement measurement, a velocity measurement, or an acceleration measurement. The movement measurement is based on the position and/or a change in position of the head of the user. The velocity measurement is based on the change in position of the head of the user as a function of time and the acceleration measurement is based on the rate of change in position of the head of the user as a function of time.

The second movement measurement of the head of the user may be triaxial. As such, the second movement measurement of the head of the user may include a displacement, a velocity rate, and/or an acceleration rate of the head of the user relative to the vehicle 102 along the three axes. As an example, the radar sensor 123 may be a multiple input, multiple output millimeter wave radar. As an example, the radar sensor 123 located in the vehicle 102 can measure the second movement measurement of the head of the user. The radar sensor 123 may then transmit the second movement measurement as a function of time to the control module 220.

The control module 220 may then determine the movement measurement of the head of the user relative to the earth or any suitable stationary object by combining the first movement measurement and the second movement measurement. As an example, the control module 220 may determine the movement measurement of the head of the user relative to the earth by summing up the first movement measurement and the second movement measurement. As another example, the control module 220 may movement measurement of the head of the user relative to the earth by comparing the first movement measurement to the second movement measurement using any suitable machine learning methods.

The control module 220 may then apply the movement measurement of the head of the user relative to the earth to the MSI model 230 to predict whether the user is experiencing motion sickness and/or the severity of the motion sickness the user is experiencing.

In one embodiment, the control module 220 may include instructions that, when executed by the processor(s) 110, cause the processor(s) 110 to receive a motion sickness sensitivity score from the user and determine whether the user is experiencing motion sickness further based on the motion sickness sensitivity score. As such, the control module 220 may request the motion sickness sensitivity score from the user through any suitable interface such as a mobile device or the input system in the vehicle 102. As an example, the control module 220 may request the user provide a motion sensitivity score (e.g., a score between 0 and 10, 0 being no motion sensitivity and 10 being very high motion sensitivity). As another example, the control module 220 may prompt the user by asking the user to rank (e.g., between 0 and 5) the likelihood that user will experience motion sickness during a vehicle ride and the severity of the user's motion sickness. The control module 220 may utilize the ranking to determine a motion sensitivity score for the user. As another example, the control module 220 may prompt the user for the sex and age of the user and the control module 220 may utilize the information to determine a motion sensitivity score for the user. The control module 220 may then apply the movement measurement of the head of the user relative to the earth in addition to motion sensitivity score to the MSI model 230 to predict whether the user is experiencing motion sickness and/or the severity of the motion sickness the user is experiencing. As an example, the control module 220 may utilize the model sensitivity score as a weighting factor for the inputs to the MSI model 230.

In one embodiment, the control module 220 may include instructions that, when executed by the processor(s) 110, cause the processor(s) 110 to determine whether a second user in the vehicle 102 is experiencing motion sickness based on the first movement measurement and a third movement measurement of a head of the second user in the vehicle 102 using a second radar sensor 123, determine which of the first user or the second user is experiencing more severe motion sickness, and generate a drop off schedule based on which of the first user or the second user is experiencing more severe motion sickness. The drop off schedule is a schedule of the order in which the users (or passengers) in the vehicle 102 are to be dropped off at various destinations.

The control module 220 may determine the number of users in the vehicle 102 using any suitable method. As an example, the control module 220 may receive sensor data 119 indicating the number of users in the vehicle 102. In a case where there is more than one user in the vehicle 102, the control module 220 may receive a movement measurement of a head of the other user(s) in the vehicle 102 using the same or another radar sensor 123. As an example, the second radar sensor 123 may capture the head movements of the second user in the vehicle 102. In other words, the second radar sensor 123 may capture the third movement measurement of the head of the second user. The control module 220 may receive the third movement measurement of the head of the second user in the vehicle 102 from the second radar sensor 123. The control module 220 may then determine the movement measurement of the head of the second user relative to the earth or any suitable stationary object by combining the first movement measurement and the third movement measurement. The control module 220 may then apply the movement measurement of the head of the second user relative to the earth to the MSI model 230 to predict whether the second user is experiencing motion sickness and/or the severity of the motion sickness the second user is experiencing. The control module 220 may also determine a model sensitivity score for the second user and apply the motion sensitivity score along with the first movement measurement and the third movement measurement to the MSI model 230 to determine whether the second user is experiencing motion sickness and/or the severity of the motion sickness the second user is experiencing.

The control module 220 may assign a first value to the severity of the motion sickness of the first user and a second value to the severity of the motion sickness of the second user. The control module 220 may then determine which user is experiencing a more severe motion sickness and which user is experiencing a less severe motion sickness. In the case where the first user and the second user are travelling to two different destinations, the control module 220 may generate a drop off schedule prioritizing dropping off the user with the more severe motion sickness before the user with the less severe motion sickness. As such, the control module 220 may include the severity of motion sickness of the users as one of the factors used to determine the order in which the users are dropped off.

In one embodiment, the control module 220 may include instructions that, when executed by the processor(s) 110, cause the processor(s) 110 to, in response to determining whether the user is experiencing motion sickness, activate mitigation control to alleviate the effects and/or the severity of the motion sickness on the user. The mitigation control may include adjusting a vehicle cabin temperature, adjusting a vehicle seat recline angle, opening a vehicle window, adjusting a window tint, activating a seat ventilation system, or adjusting vehicle driving style. As such and as an example, the control module 220 may determine the current value for the vehicle cabin temperature and may instruct the HVAC system 148 to increase or decrease the vehicle cabin temperature to alleviate the severity of the motion sickness on the user(s). As another example, the control module 220 may determine the current recline angle of the seat in which the user is sitting and may instruct a vehicle seat control system 149 to adjust the vehicle seat recline angle. As another example, the control module 220 may instruct a window control system 151 to increase or decrease the opening of the vehicle window(s) and/or increase or decrease the tint of the vehicle window(s). As another example, the control module 220 may activate or adjust the seat ventilation system 150 to change the rate and/or temperature of air flowing of the seat that the user is sitting on. As another example and in a case where the vehicle is being semi-autonomously or fully autonomously controlled, the control module 220 may instruct the autonomous vehicle system 160 to adjust the driving style. As another example, the autonomous vehicle system 160 may adjust the driving style by changing the route of travel, reducing the speed of travel, the sharpness of turns, and/or the vehicle response time to sudden breaks. The control module 220 may determine which mitigation control(s) to activate based on the effectiveness of the mitigation control.

Figure 3:
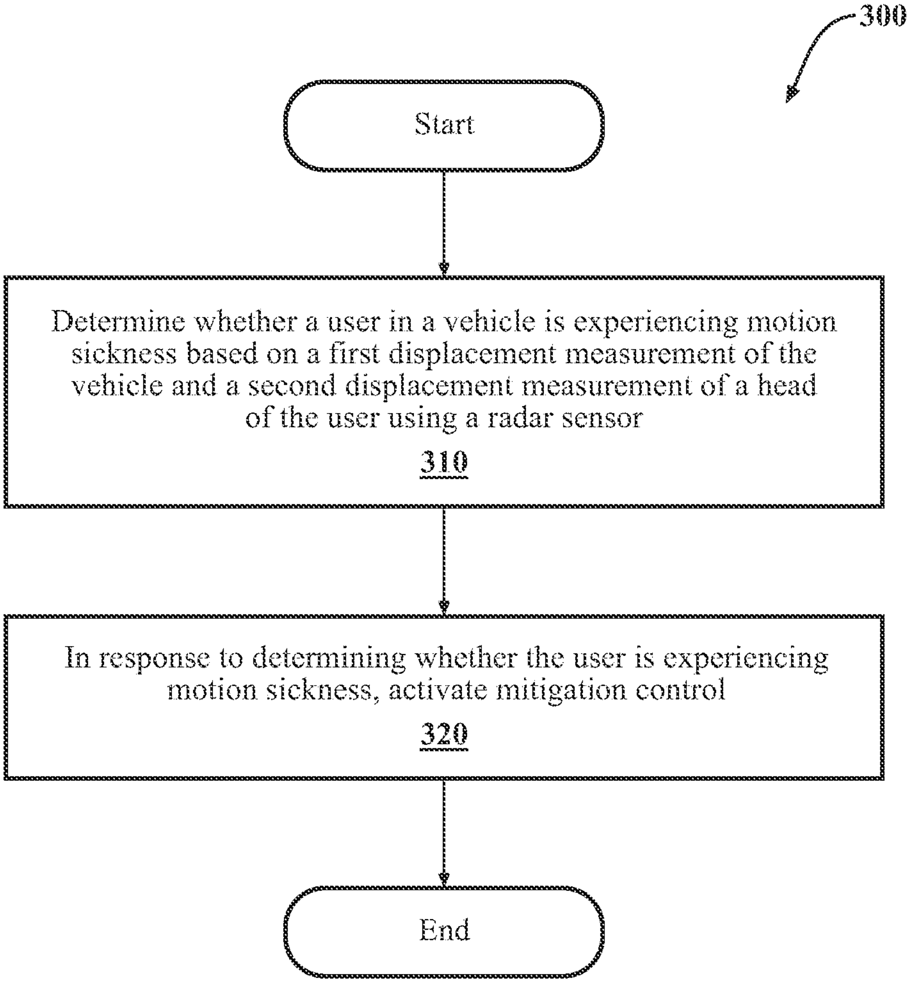
FIG. 3 is an example of a method for determining whether a user is experiencing motion sickness.

FIG. 3 illustrates a method 300 for determining whether a user in a vehicle 102 is experiencing motion sickness. The method 300 will be described from the viewpoint of the vehicle 102 of FIG. 1 and the motion sickness mitigation system 100 of FIGS. 1 and 2. However, the method 300 may be adapted to be executed in any one of several different situations and not necessarily by the vehicle 102 of FIG. 1 and/or the motion sickness mitigation system 100 of FIGS. 1 and 2.

At step 310, the control module 220 may cause the processor(s) 110 to determine whether a user in a vehicle 102 is experiencing motion sickness based on a first movement measurement of the vehicle 102 and a second movement measurement of a head of the user using a radar sensor 123. As previously mentioned, the control module 220 may receive sensor data 119 that includes the first movement measurement of the vehicle 102. The first movement measurement of the vehicle 102 may be triaxial and may be detected by, as an example, a triaxial accelerometer located in the vehicle 102. The control module 220 may receive sensor data 119 that include the second movement measurement of the head of the user. The second movement measurement of the head of the user may be triaxial and may be detected by a radar sensor 123 located in the vehicle 102. As an example, the radar sensor 123 may be a multiple input, multiple output millimeter wave radar.

The control module 220 may combine the first movement measurement and the second movement measurement to determine the absolute movement measurement of the head of the user (i.e., the movement measurement of the head of the user relative to a stationary object).

The control module 220 may then apply the absolute movement measurement of the head of the user to the MSI model 230 to predict whether the user is experiencing or likely to experience motion sickness. Additionally, the control module 220 may receive a motion sickness sensitivity score from the user which indicates how susceptible the user is to motion sickness. The control module 220 may apply the motion sickness score as an input to the MSI model 230.

Additionally, the control module 220 may determine whether multiple users in the vehicle 102 are experiencing motion sickness. As such and as an example for a second user, the control module 220 may receive sensor data 119 that includes a third movement measurement for the head of the second user. The control module 220 may combine the first movement measurement and the third movement measurement to determine the absolute movement measurement of the head of the second user. The control module 220 may then apply the absolute movement measurement of the head of the second user to the MSI model 230 to predict whether the second user is experiencing or likely to experience motion sickness.

At step 320, the control module 220 may cause the processor(s) 110 to, in response to determining whether the user is experiencing motion sickness, activate mitigation control. As previously disclosed, the mitigation control may include adjusting a vehicle cabin temperature, adjusting a vehicle seat recline angle, opening a vehicle window, adjusting a window tint, activating a seat ventilation system, and/or adjusting vehicle driving style. Further, the control module 220 may generate a drop off schedule for the multiple users based on the severity of the users' motion sickness.

Figure 4A:
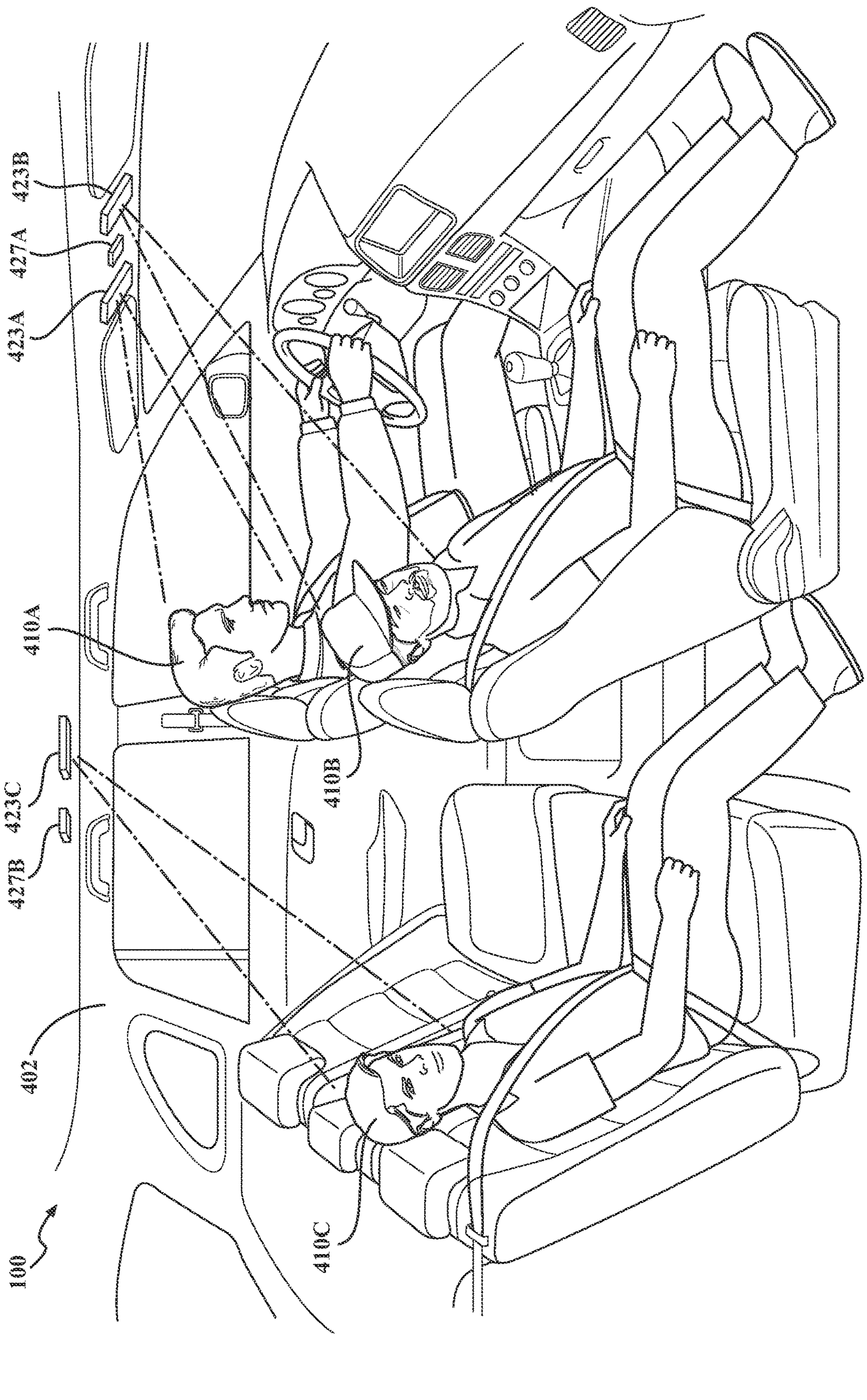
FIGS. 4A-4C illustrate a motion sickness detection and mitigation scenario.
Figure 4B:
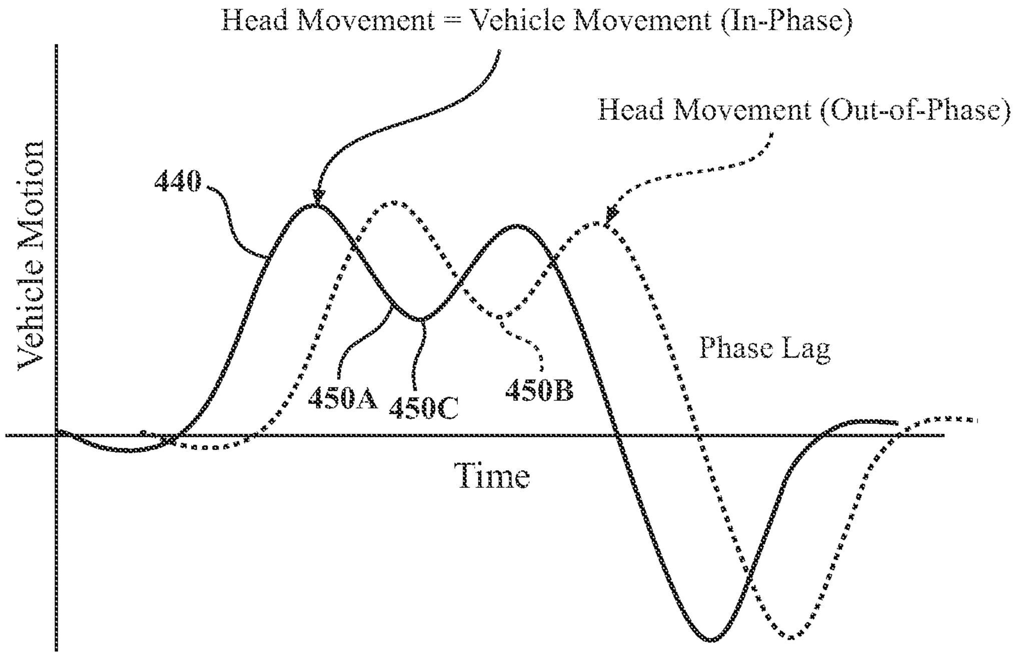
Figure 4C:
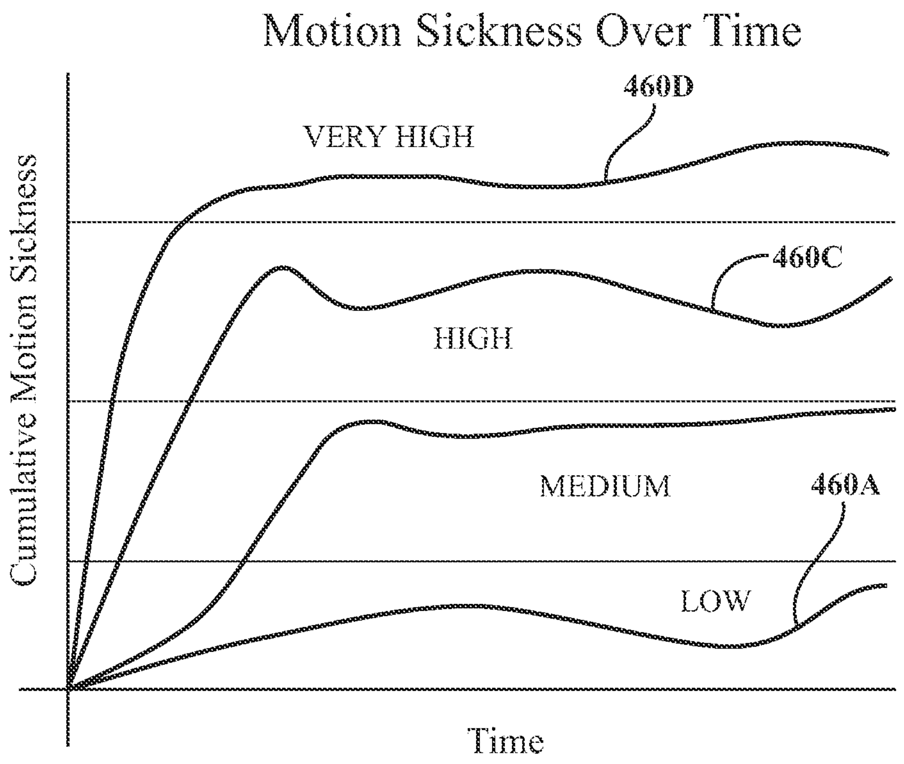

A non-limiting example of the operation of the motion sickness mitigation system 100, and/or one or more of the methods will now be described in relation to FIGS. 4A-4C. FIGS. 4A-4C illustrate a motion sickness detection and mitigation scenario.

FIG. 4A shows three users, a driver 410A, a first passenger 410B, and a second passenger 410C (collectively known as 410), in a vehicle 402 (which is similar to vehicle 102). The vehicle 402 includes three radar sensors, a first radar sensor 423A, a second radar sensor 423B, and a third radar sensor 423C, inside the vehicle 402. Additionally, the vehicle 402 includes two triaxial accelerometers, a first triaxial accelerometer 427A that is proximate to the first radar sensor 423A and the second radar sensor 423B, and a second accelerometer 427B that is proximate to the third radar sensor 423C. The triaxial accelerometers 427A. 427B (collectively known as 427) detect the movements of the vehicle 402. The first radar sensor 423A is directed at and detects the movement of the head of the driver 410A. The second radar sensor 423B is directed at and detects the movement of the head of the first passenger 410B. The third radar sensor 423C is directed at and detects the movement of the head of the second passenger 410C.

The motion mitigation system 100, or more specifically, the control module 220 receives sensor data 119 that includes the movement measurement of the vehicle 402, and the movement measurements of the users 410. The control module 220 determines the absolute movement measurements for the users 410. More specifically, the control module determines the absolute movement measurement of the driver 410A using the first radar sensor 423A and the first triaxial accelerometer 427A, the absolute movement measurement of the first passenger 410B using the second radar sensor 423B and the first triaxial accelerometer 427A, and the absolute movement of the second passenger 410C using the third radar sensor 423C and the second triaxial accelerometer 427B.

FIG. 4B shows the vehicle movement 440 and the head movement 450 of the users 410. The head movements 450A, 450C of the driver 410A and the second passenger 410C are in phase with the vehicle movement 440 while the head movements 450B of the first passenger 410B are out of phase with the vehicle movement 440. The control module 220 determines the absolute movement measurements for the users 410 and inputs the absolute movement measurements into the MSI model 230, which predicts the likelihood that the users 410 are experiencing motion sickness and the severity of the motion sickness. The control module 220 then associates a value indicating the severity of motion sickness with each of the users 410. The control module 220 then ranks the users 410 based on the severity of the users' motion sickness. In this example and as shown in FIG. 4C, the first passenger 410B is experiencing the most severe motion sickness 460D, the second passenger 410C is experiencing the least severe motion sickness 460A, and the driver 410A is in between, experiencing motion sickness 460C that is less severe motion sickness than the first passenger 410B but more severe motion sickness than the second passenger 410C.

In this example and to alleviate the impact of the motion sickness on the users 410, the control module 220 implements varying mitigation measures based on the user 410 and the severity of motion sickness on the user 410. In this example (not shown), the control module 220 activates the HVAC system 148 to adjust the vehicle cabin temperature. Additionally, the control module 220 activates the vehicle seat control system 149 for the seats occupied by the passengers 410B, 410C to adjust the vehicle seat recline angle such that the passengers 410B, 410C are sitting in a more reclined position. The control module 220 activates the seat ventilation system 150 for the three seats occupied by the three users 410. The control module 220 varies the rate of airflow and the air temperature for each seat based on the severity of the user's motion sickness. The motion sickness mitigation system 100 then provides routing information to the driver 410A that prioritizes dropping off the first passenger 410B before the second passenger 410C.

FIG. 1 will now be discussed in full detail as an example environment within which the system and methods disclosed herein may operate. In some instances, the vehicle 102 is configured to switch selectively between an autonomous mode, one or more semi-autonomous operational modes, and/or a manual mode. Such switching can be implemented in a suitable manner, now known or later developed. "Manual mode" means that all of or a majority of the navigation and/or maneuvering of the vehicle is performed according to inputs received from a user (e.g., human driver). In one or more arrangements, the vehicle 102 can be a conventional vehicle that is configured to operate in only a manual mode.

In one or more embodiments, the vehicle 102 is an autonomous vehicle. As used herein, “autonomous vehicle” refers to a vehicle that operates in an autonomous mode. “Autonomous mode” refers to navigating and/or maneuvering the vehicle 102 along a travel route using one or more computing systems to control the vehicle 102 with minimal or no input from a human driver. In one or more embodiments, the vehicle 102 is highly automated or completely automated. In one embodiment, the vehicle 102 is configured with one or more semi-autonomous operational modes in which one or more computing systems perform a portion of the navigation and/or maneuvering of the vehicle along a travel route, and a vehicle operator (i.e., driver) provides inputs to the vehicle to perform a portion of the navigation and/or maneuvering of the vehicle 102 along a travel route.

The vehicle 102 can include one or more processors 110. In one or more arrangements, the processor(s) 110 can be a main processor of the vehicle 102. For instance, the processor(s) 110 can be an electronic control unit (ECU). The vehicle 102 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory). EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term “operatively connected.” as used throughout this description, can include direct or indirect connections, including connections without direct physical contact.

In one or more arrangements, the one or more data stores 115 can include sensor data 119. In this context. “sensor data” means any information about the sensors that the vehicle 102 is equipped with, including the capabilities and other information about such sensors. As will be explained below, the vehicle 102 can include the sensor system 120. The sensor data 119 can relate to one or more sensors of the sensor system 120. As an example, in one or more arrangements, the sensor data 119 can include information on one or more vehicle sensors 121 and/or environment sensors 122 of the sensor system 120.

In some instances, at least a portion of the sensor data 119 can be located in one or more data stores 115 located onboard the vehicle 102. Alternatively, or in addition, at least a portion of the sensor data 119 can be located in one or more data stores 115 that are located remotely from the vehicle 102.

The vehicle 102 can include an input system 130. An “input system” includes any device, component, system, element or arrangement or groups thereof that enable information/data to be entered into a machine. The input system 130 can receive an input from a user (e.g., a driver or a passenger). As an example, the input system can receive information from the user relating to the user’s sensitivity and/or susceptibility to motion sickness. The vehicle 102 can include an output system 135. An “output system” includes any device, component, or arrangement or groups thereof that enable information/data to be presented to a user (e.g., a person, a vehicle passenger, etc.) such as a display interface.

The navigation system 147 can include one or more devices, applications, and/or combinations thereof, now known or later developed, configured to determine the geographic location of the vehicle 102 and/or to determine a travel route for the vehicle 102. The navigation system 147 can include one or more mapping applications to determine a travel route for the vehicle 102. The navigation system 147 can include a global positioning system, a local positioning system or a geolocation system.

The vehicle 102 can include one or more autonomous driving systems 160. The autonomous driving system 160 can include one or more devices, applications, and/or combinations thereof, now known or later developed, configured to control the movement, speed, maneuvering, heading, direction, etc. of the vehicle 102. The autonomous driving system 160 can include one or more driver assistance systems such as a lane keeping system, a lane centering system, a collision avoidance system, and/or a driver monitoring system.

The autonomous driving system(s) 160 can be configured to receive data from the sensor system 120 and/or any other type of system capable of capturing information relating to the vehicle 102 and/or the external environment of the vehicle 102. In one or more arrangements, the autonomous driving system(s) 160 can use such data to generate one or more driving scene models. The autonomous driving system(s) 160 can determine position and velocity of the vehicle 102. The autonomous driving system(s) 160 can determine the location of obstacles, obstacles, or other environmental features including traffic signs, trees, shrubs, neighboring vehicles, pedestrians, etc.

The autonomous driving system(s) 160 can be configured to receive, and/or determine location information for obstacles within the external environment of the vehicle 102 for use by the processor(s) 110, and/or one or more of the modules described herein to estimate position and orientation of the vehicle 102, vehicle position in global coordinates based on signals from a plurality of satellites, or any other data and/or signals that could be used to determine the current state of the vehicle 102 or determine the position of the vehicle 102 with respect to its environment for use in either creating a map or determining the position of the vehicle 102 in respect to map data.

The autonomous driving system(s) 160 either independently or in combination with the motion sickness mitigation system 100 can be configured to determine travel path(s), current autonomous driving maneuvers for the vehicle 102, future autonomous driving maneuvers and/or modifications to current autonomous driving maneuvers based on data acquired by the sensor system 120, driving scene models, and/or data from any other suitable source such as determinations from the sensor data 119. “Driving maneuver” means one or more actions that affect the movement of a vehicle. Examples of driving maneuvers include accelerating, decelerating, braking, turning, moving in a lateral direction of the vehicle 102, changing travel lanes, merging into a travel lane, and/or reversing, just to name a few possibilities. The autonomous driving system(s) 160 can be configured to implement determined driving maneuvers. The autonomous driving system(s) 160 can cause, directly or indirectly, such autonomous driving maneuvers to be implemented. As used herein, “cause” or “causing” means to make, command, instruct, and/or enable an event or action to occur or at least be in a state where such event or action may occur, either in a direct or indirect manner. The autonomous driving system(s) 160 can be configured to execute various vehicle functions and/or to transmit data to, receive data from, interact with, and/or control the vehicle 102 or one or more systems thereof (e.g., one or more of vehicle systems 140).

The processor(s) 110, the motion sickness mitigation system 100, and/or the autonomous driving system(s) 160 can be operatively connected to communicate with the various vehicle systems 140 and/or individual components thereof. For example, returning to FIG. 1, the processor(s) 110, the motion sickness mitigation system 100, and/or the autonomous driving system(s) 160 can be in communication to send and/or receive information from the various vehicle systems 140 to control the movement, speed, maneuvering, heading, direction, etc. of the vehicle 102. The processor(s) 110, the motion sickness mitigation system 100, and/or the autonomous driving system(s) 160 may control some or all of these vehicle systems 140 and, thus, may be partially or fully autonomous.

The processor(s) 110, the motion sickness mitigation system 100, and/or the autonomous driving system(s) 160 may be operable to control the navigation and/or maneuvering of the vehicle 102 by controlling one or more of the vehicle systems 140 and/or components thereof. As an example, when operating in an autonomous mode, the processor(s) 110, the motion sickness mitigation system 100, and/or the autonomous driving system(s) 160 can control the direction and/or speed of the vehicle 102. As another example, the processor(s) 110, the motion sickness mitigation system 100, and/or the autonomous driving system(s) 160 can activate, deactivate, and/or adjust the parameters (or settings) of the one or more driver assistance systems. The processor(s) 110, the motion sickness mitigation system 100, and/or the autonomous driving system(s) 160 can cause the vehicle 102 to accelerate (e.g., by increasing the supply of fuel provided to the engine), decelerate (e.g., by decreasing the supply of fuel to the engine and/or by applying brakes) and/or change direction (e.g., by turning the front two wheels). As used herein, “cause” or “causing” means to make, force, compel, direct, command, instruct, and/or enable an event or action to occur or at least be in a state where such event or action may occur, either in a direct or indirect manner.

The vehicle 102 can include one or more actuators 155. The actuators 155 can be any element or combination of elements operable to modify, adjust and/or alter one or more of the vehicle systems 140 or components thereof to responsive to receiving signals or other inputs from the processor(s) 110 and/or the autonomous driving system(s) 160. Any suitable actuator can be used. For instance, the one or more actuators 155 can include motors, pneumatic actuators, hydraulic pistons, relays, solenoids, and/or piezoelectric actuators, just to name a few possibilities.

The vehicle 102 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in the figures, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase “computer-readable storage medium” means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, modules, as used herein, include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk. C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A method comprising:

determining whether a user in a vehicle is experiencing motion sickness based on at least a phasal difference between a first movement measurement of the vehicle and a second movement measurement of a head of the user using a radar sensor;

in response to determining whether the user is experiencing motion sickness, activating mitigation control;

determining whether a second user in the vehicle is experiencing motion sickness based on the first movement measurement and a third movement measurement of a head of the second user using a second radar;

determining which of the user or the second user is experiencing more severe motion sickness; and generating a drop off schedule based on which of the user or the second user is experiencing more severe motion sickness.

2. The method of claim 1, wherein the first movement measurement and the second movement measurement are based on one or more of:

a movement measurement;

a velocity measurement; or an acceleration measurement.

3. The method of claim 1, wherein the first movement measurement and the second movement measurement are triaxial.

4. The method of claim 1, wherein the radar sensor is multiple input, multiple output millimeter wave radar.

5. The method of claim 1, further comprising:

receiving a motion sickness sensitivity score from the user; and wherein determining whether the user is experiencing motion sickness is further based on the motion sickness sensitivity score.

6. The method of claim 1, wherein the mitigation control includes at least one of:

adjusting a vehicle cabin temperature;

adjusting a vehicle seat recline angle;

opening a vehicle window;

adjusting a window tint;

activating a seat ventilation system; or adjusting vehicle driving style.

7. A system, comprising:

a processor; and a memory storing machine-readable instructions that, when executed by the processor, cause the processor to:

determine whether a user in a vehicle is experiencing motion sickness based on at least a phasal difference between a first movement measurement of the vehicle and a second movement measurement of a head of the user using a radar sensor;

in response to determining whether the user is experiencing motion sickness, activate mitigation control;

determine whether a second user in the vehicle is experiencing motion sickness based on the first movement measurement and a third movement measurement of a head of the second user using a second radar;

determine which of the user or the second user is experiencing more severe motion sickness; and generate a drop off schedule based on which of the user or the second user is experiencing more severe motion sickness.

8. The system of claim 7, wherein the first movement measurement and the second movement measurement are based on one or more of:

a movement measurement;

a velocity measurement; or an acceleration measurement.

9. The system of claim 7, wherein the first movement measurement and the second movement measurement are triaxial.

10. The system of claim 7, wherein the radar sensor is multiple input, multiple output millimeter wave radar.

11. The system of claim 7, wherein the machine-readable instructions further include instructions that when executed by the processor cause the processor to:

receive a motion sickness sensitivity score from the user; and determine whether the user is experiencing motion sickness further based on the motion sickness sensitivity score.

12. The system of claim 7, wherein the mitigation control includes at least one of:

adjusting a vehicle cabin temperature;

adjusting a vehicle seat recline angle;

opening a vehicle window;

adjusting a window tint;

activating a seat ventilation system; or adjusting vehicle driving style.

13. A non-transitory computer-readable medium including instructions that when executed by a processor cause the processor to:

determine whether a user in a vehicle is experiencing motion sickness based on at least a phasal difference between a first movement measurement of the vehicle and a second movement measurement of a head of the user using a radar sensor;

in response to determining whether the user is experiencing motion sickness, activate mitigation control;

determine whether a second user in the vehicle is experiencing motion sickness based on the first movement measurement and a third movement measurement of a head of the second user using a second radar;

determine which of the user or the second user is experiencing more severe motion sickness; and generate a drop off schedule based on which of the user or the second user is experiencing more severe motion sickness.

14. The non-transitory computer-readable medium of claim 13, wherein the first movement measurement and the second movement measurement are based on one or more of:

a movement measurement;

a velocity measurement; or an acceleration measurement.

15. The non-transitory computer-readable medium of claim 13, wherein the first movement measurement and the second movement measurement are triaxial.

16. The non-transitory computer-readable medium of claim 13, wherein the radar sensor is multiple input, multiple output millimeter wave radar.

17. The non-transitory computer-readable medium of claim 13, wherein the instructions further include instructions that when executed by the processor cause the processor to:

receive a motion sickness sensitivity score from the user; and determine whether the user is experiencing motion sickness further based on the motion sickness sensitivity score.

18. The non-transitory computer-readable medium of claim 13, wherein the mitigation control includes at least one of:

adjusting a vehicle cabin temperature;

adjusting a vehicle seat recline angle;

opening a vehicle window;

adjusting a window tint;

activating a seat ventilation system; or adjusting vehicle driving style.

* * * * *